(12) United States Patent
Sinha et al.

(10) Patent No.: US 11,462,123 B2
(45) Date of Patent: Oct. 4, 2022

(54) SYSTEM AND METHOD FOR DIGITIZED DIGIT SYMBOL SUBSTITUTION TEST

(71) Applicant: Tata Consultancy Services Limited, Mumbai (IN)

(72) Inventors: Aniruddha Sinha, Kolkata (IN); Debatri Chatterjee, Kolkata (IN); Kingshuk Chakravarty, Kolkata (IN); Rahul Dasharath Gavas, Kolkata (IN); Pratyusha Das, Kolkata (IN); Uttama Lahiri, Gandhinagar (IN)

(73) Assignee: TATA CONSULTANCY SERVICES LIMITED, Mumbai (IN)

( * ) Notice: Subject to any disclaimer, the term of this patent is extended or adjusted under 35 U.S.C. 154(b) by 826 days.

(21) Appl. No.: 16/343,691

(22) PCT Filed: Oct. 18, 2017

(86) PCT No.: PCT/IB2017/056483
§ 371 (c)(1),
(2) Date: Apr. 19, 2019

(87) PCT Pub. No.: WO2018/073769
PCT Pub. Date: Apr. 26, 2018

(65) Prior Publication Data
US 2019/0385475 A1    Dec. 19, 2019

(30) Foreign Application Priority Data
Oct. 21, 2016    (IN) .............................. 201621036029

(51) Int. Cl.
*G09B 19/00*    (2006.01)
*G09B 7/00*    (2006.01)
*G06N 7/00*    (2006.01)

(52) U.S. Cl.
CPC .............. *G09B 19/00* (2013.01); *G06N 7/005* (2013.01); *G09B 7/00* (2013.01)

(58) Field of Classification Search
CPC ........... G09B 19/00; G09B 7/00; G06N 7/005
(Continued)

(56) References Cited

U.S. PATENT DOCUMENTS

2004/0111438 A1    6/2004    Chitrapura et al.
2004/0229198 A1*   11/2004   Boyd ....................... G09B 7/00
                                                         434/236

(Continued)

OTHER PUBLICATIONS

International Search Report dated Mar. 9, 2018, in International Application PCT/IB2017/056483; 2 pages.

(Continued)

*Primary Examiner* — Thomas J Hong
(74) *Attorney, Agent, or Firm* — Finnegan, Henderson, Farabow, Garrett & Dunner LLP (57) ABSTRACT

System and method for digitized digit symbol substitution test (DSST) are disclosed. In an example, a display area of a digitized DSST device is partitioned into multiple bins. Further, a series of number symbol pairs is displayed as a lookup table on top of the display, termed as a lookup area. Furthermore, a question and answer (QA) pair corresponding to the series of number symbol pairs to an examinee in multiple trials. In addition, feature values for the QA pair are computed in each of the multiple bins in the trials, wherein the feature values comprise a response time and an accuracy of response by the examinee. Moreover, probabilities of the feature values are determined in each of the multiple bins. Also, an entropy value based on the probabilities of the feature values is computed in each of the multiple bins providing information on distribution.

15 Claims, 7 Drawing Sheets

(58) Field of Classification Search
USPC .......................................................... 434/236
See application file for complete search history.

(56) References Cited

U.S. PATENT DOCUMENTS

| | | | |
|---|---|---|---|
| 2007/0166675 A1* | 7/2007 | Atkins | G09B 7/04 434/236 |
| 2010/0092929 A1 | 4/2010 | Hallowell et al. | |
| 2011/0270123 A1 | 11/2011 | Reiner | |
| 2016/0022136 A1 | 1/2016 | Ettenhofer et al. | |

OTHER PUBLICATIONS

Written Opinion dated Mar. 9, 2018, in International Application PCT/IB2017/056483; 3 pages.

* cited by examiner

SYSTEM AND METHOD FOR DIGITIZED DIGIT SYMBOL SUBSTITUTION TEST

CROSS REFERENCE TO RELATED APPLICATIONS AND PRIORITY

The present invention This is a U.S. National Stage Filing under 35 U.S.C. § 371 and claims priority from International Application No. PCT/IB2017/056483 filed on. Oct. 18, 2017 which claims priority to Indian Application No. 201621036029, filed in India on Oct. 21, 2016. The entire contents of the aforementioned applications are incorporated herein by reference.

TECHNICAL FIELD

The embodiments herein generally relate to digit symbol substitution test (DSST) and, more particularly, to system and method for visual Bayesian data fusion.

BACKGROUND

Digit Symbol Substitution Test (DSST) is a neuropsychological test sensitive to brain damage, dementia, age and depression. However, the test is not sensitive to the location of the brain damage except for damage comprising part of the visual field. Typically, the DSST consists of 9 digits and corresponding symbols. A user or an examinee should remember where each symbol matches a digit. Initially, the examinee is shown a key containing numbers from 1 to 9 and under each number, a corresponding symbol is given. Further, the examinee is shown a series of boxes containing numbers in top boxes and the boxes below the top boxes are kept as blank. After a short period of time, the examinee is asked to copy the corresponding symbol under each number. A score is then calculated and the score is the number of correct items completed within the prescribed time limit. The initial rounds of the DSST tests are simple and the later rounds are challenging due to time exhaustion. The most obvious application of the DSST is to memory. In clinical setting, DSST is used to test brain injury, especially for athletes suffering concussions.

In the conventional methods like pen and paper DSST, the assessment is purely based on the correct matches done within the given time interval. The test does not consider the gradual changes occurring in the response time, attention, working memory and visuo-motor coordination. Also, the focus is mainly on the results pertaining to the entire task duration.

SUMMARY

The following presents a simplified summary of some embodiments of the disclosure in order to provide a basic understanding of the embodiments. This summary is not an extensive overview of the embodiments. It is not intended to identify key/critical elements of the embodiments or to delineate the scope of the embodiments. Its sole purpose is to present some embodiments in a simplified form as a prelude to the more detailed description that is presented below.

In view of the foregoing, an embodiment herein provides methods and systems for digitized digit symbol substitution test (DSST) are disclosed. In one aspect, a processor-implemented method includes steps of: partitioning a display area of a digitized digit symbol substitution test (DSST) device into multiple bins based on distance and degree from a center position of the display area; displaying a series of number symbol pairs as a lookup table on top of the display, termed as a lookup area; displaying a question and answer (QA) pair corresponding to the series of number symbol pairs to an examinee in multiple trials, wherein the location of the QA pair is changed in each of the multiple trials so that equal number of pairs are present in the multiple bins; computing feature values for the QA pair in each of the multiple bins in the multiple trials, wherein the feature values comprise a response time and an accuracy of response by the examinee; determining probabilities of the feature values in each of the multiple bins; and computing an entropy value based on the probabilities of the feature values in each of the multiple bins, wherein the entropy value provides information on distribution of the feature values in the display area.

In another aspect, a system for digitized digit symbol substitution test (DSST) is disclosed. The system includes a DSST device including one or more memories; and one or more hardware processors, the one or more memories coupled to the one or more hardware processors, wherein the one or more hardware processors are capable of executing programmed instructions stored in the one or more memories to: partition a display area in the DSST device into multiple bins based on distance and degree from a center position of the display area; display a series of number symbol pairs as a lookup table on top of the display, termed as a lookup area; display a question and answer (QA) pair corresponding to the series of number symbol pairs to an examinee in multiple trials, wherein the location of the QA pair is changed in each of the multiple trials so that equal number of pairs are present in the multiple bins; compute feature values for the QA pair in each of the multiple bins in the multiple trials, wherein the feature values comprise a response time and an accuracy of response by the examinee; determine probabilities of the feature values in each of the multiple bins; and compute an entropy value based on the probabilities of the feature values in each of the multiple bins, wherein the entropy value provides information on distribution of the feature values in the display area.

In yet another aspect, a non-transitory computer-readable medium having embodied thereon a computer program for executing a method for digitized digit symbol substitution test (DSST) is disclosed. The method includes steps of: partitioning a display area of a digitized digit symbol substitution test (DSST) device into multiple bins based on distance and degree from a center position of the display area; displaying a series of number symbol pairs as a lookup table on top of the display, termed as a lookup area; displaying a question and answer (QA) pair corresponding to the series of number symbol pairs to an examinee in multiple trials, wherein the location of the QA pair is changed in each of the multiple trials so that equal number of pairs are present in the multiple bins; computing feature values for the QA pair in each of the multiple bins in the multiple trials, wherein the feature values comprise a response time and an accuracy of response by the examinee; determining probabilities of the feature values in each of the multiple bins; and computing an entropy value based on the probabilities of the feature values in each of the multiple bins, wherein the entropy value provides information on distribution of the feature values in the display area.

It should be appreciated by those skilled in the art that any block diagram herein represents conceptual views of illustrative systems embodying the principles of the present subject matter. Similarly, it is appreciated that any flow charts, flow diagrams, state transition diagrams, pseudo code, and the like represent various processes which may be substantially represented in computer readable medium and so executed by a computing device or processor, whether or not such computing device or processor is explicitly shown.

BRIEF DESCRIPTION OF THE FIGURES

The detailed description is described with reference to the accompanying figures. In the figures, the left-most digit(s) of a reference number identifies the figure in which the reference number first appears. The same numbers are used throughout the drawings to reference like features and modules.

It should be appreciated by those skilled in the art that any block diagrams herein represent conceptual views of illustrative systems and devices embodying the principles of the present subject matter. Similarly, it will be appreciated that any flow charts, flow diagrams, and the like represent various processes which may be substantially represented in computer readable medium and so executed by a computer or processor, whether or not such computer or processor is explicitly shown.

DETAILED DESCRIPTION

The embodiments herein and the various features and advantageous details thereof are explained more fully with reference to the non-limiting embodiments that are illustrated in the accompanying drawings and detailed in the following description. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

The methods and systems are not limited to the specific embodiments described herein. In addition, the method and system can be practiced independently and separately from other modules and methods described herein. Each device element/module and method can be used in combination with other elements/modules and other methods.

The manner, in which the system and method for digitized digit symbol substitution test (DSST), has been explained in details with respect to the FIGS. 1 through 7. While aspects of described methods and systems for digitized DSST can be implemented in any number of different systems, utility environments, and/or configurations, the embodiments are described in the context of the following exemplary system(s).

Figure 1:
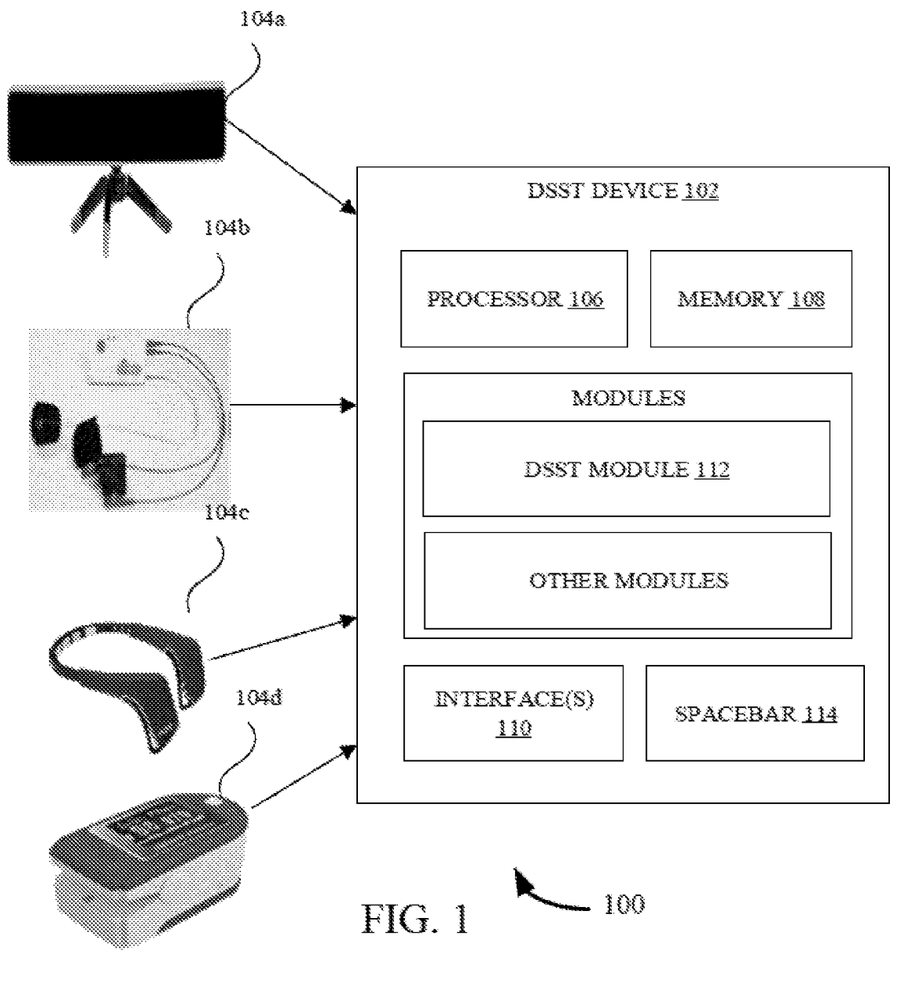
FIG. 1 illustrates a system for performing digitized digit symbol substitution test (DSST), in accordance with an example embodiment of the present disclosure.

FIG. 1 illustrates a block diagram of a system 100 for digitized DSST, in accordance with an example embodiment. In an example embodiment, the system 100 may be embodied in, or is in direct communication with a computing device. The system 100 a DSST device 102, sensors 104 communicatively coupled to the DSST device 102 and a space bar 114. For example, low cost and portable sensors 104 are connected to the digital DSST device 102 and attached to an examinee. For example, the sensors used include eye tracker, galvanic skin response (GSR) sensor, electroencephalogram (EEG) sensor, photoplethysmography (PPG) sensor and a peripheral capillary oxygen saturation (SpO2) sensor. In one embodiment, an eye tracker 104a is connected to the digitized DSST device. The eye tracker is used to identify the nature of gaze. The nature of the gaze indicates the attention, confusion, working memory related states and rest time in various locations of the stimulus. Further, the sensors attached to the examinee monitors the mental states of the examinee during the test. The sensors used during the test includes a GSR sensor 104b to determine stress during the test, n EEG sensor 104c to get the temporal data associated with the mental states of the examinee, a PPG sensor 104d to determine the heart rate variability and a SpO2 sensor.

As shown in FIG. 1, the DSST device 102 includes or is otherwise in communication with one or more hardware processors such as processor(s) 106, one or more memories such as a memory 108, a network interface unit such as a network interface unit 110 and a lookup area 112 (i.e., a display). In an embodiment, the processor 106, memory 108, and the network interface unit 110 may be coupled by a system bus such as a system bus or a similar mechanism. Although FIG. 1 shows example components of the system 100, in other implementations, the system 100 may contain fewer components, additional components, different components, or differently arranged components than depicted in FIG. 1.

The processor 106 may include circuitry implementing, among others, audio and logic functions associated with the communication, and imaging, displaying, decoding and rendering functions. For example, the processor 106 may include, but are not limited to, one or more digital signal processors (DSPs), one or more microprocessor, one or more special-purpose computer chips, one or more field-programmable gate arrays (FPGAs), one or more application-specific integrated circuits (ASICs), one or more computer(s), various analog to digital converters, digital to analog converters, and/or other support circuits. The processor 106 thus may also include the functionality to encode messages and/or data or information. The processor 106 may include, among other things, a clock, an arithmetic logic unit (ALU) and logic gates configured to support operation of the processor 102. Further, the processor 106 may include functionality to execute one or more software programs, which may be stored in the memory 108 or otherwise accessible to the processor 106.

The functions of the various elements shown in the figure, including any functional blocks labeled as "processor(s)", may be provided through the use of dedicated hardware as well as hardware capable of executing software in association with appropriate software. When provided by a processor, the functions may be provided by a single dedicated processor, by a single shared processor, or by a plurality of individual processors, some of which may be shared. Moreover, explicit use of the term "processor" should not be construed to refer exclusively to hardware capable of executing software, and may implicitly include, without limitation DSP hardware, network processor, application specific integrated circuit (ASIC), FPGA, read only memory (ROM) for storing software, random access memory (RAM), and non-volatile storage. Other hardware, conventional, and/or custom, may also be included.

The interface(s) 110 may include a variety of software and hardware interfaces, for example, interfaces for peripheral device(s), such as a keyboard, a mouse, an external memory, and a printer. The interface(s) 110 can facilitate multiple communications within a wide variety of networks and protocol types, including wired networks, for example, local area network (LAN), cable, etc., and wireless networks, such as Wireless LAN (WLAN), cellular, or satellite.

The one or more memories such as a memory 108, may store any number of pieces of information, and data, used by the system to implement the functions of the system. The memory 108 may include for example, volatile memory and/or non-volatile memory. Examples of volatile memory may include, but are not limited to volatile random access memory. The non-volatile memory may additionally or alternatively comprise an electrically erasable programmable read only memory (EEPROM), flash memory, hard drive, or the like. Some examples of the volatile memory includes, but are not limited to, random access memory, dynamic random access memory, static random access memory, and the like. Some example of the non-volatile memory includes, but are not limited to, hard disks, magnetic tapes, optical disks, programmable read only memory, erasable programmable read only memory, electrically erasable programmable read only memory, flash memory, and the like. The memory 108 may be configured to store information, data, applications, instructions or the like for enabling the system 100 to carry out various functions in accordance with various example embodiments. Additionally or alternatively, the memory 108 may be configured to store instructions which when executed by the processor 106 causes the system to behave in a manner as described in various embodiments. The memory 108 includes a DSST module 112 and/or other modules. The module 112 include routines, programs, objects, components, data structures, etc., which perform particular tasks or implement particular abstract data types. The other modules may include programs or coded instructions that supplement applications and functions of the system 100.

Figure 2:
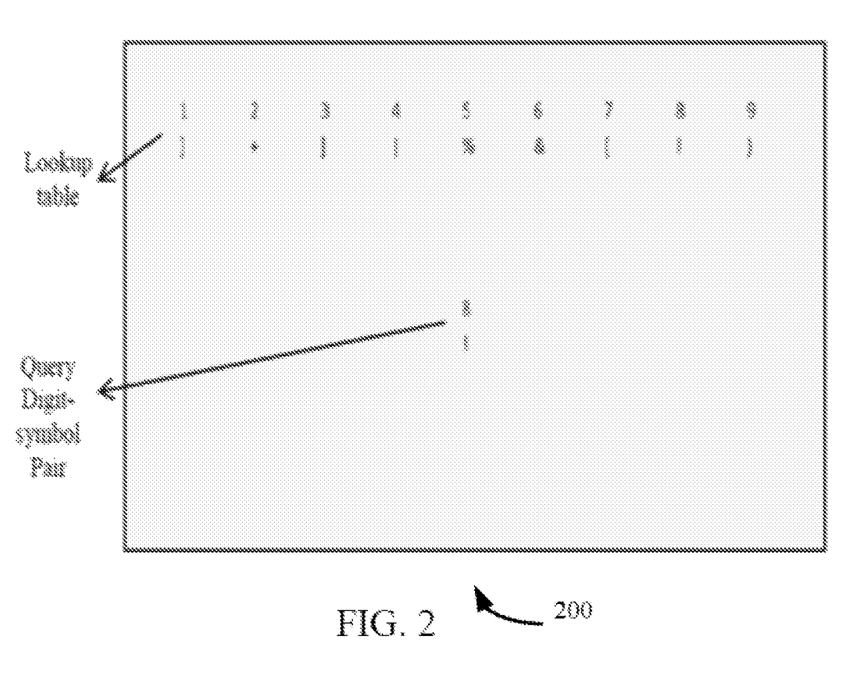
FIG. 2 depicts the version 1 of the digitization scheme of DSST, in accordance with an example embodiment of the present disclosure.

In operation, the DSST module 112 trains the examinee with a version 1 of the digitized DSST. For example, digits from 1 to 9 and their corresponding symbols are stored in a lookup table (i.e., lookup area) on a display area of the digitized DSST device 102. As shown in FIG. 2, lookup table entries 200 are fixed and placed at the top location of the display screen of the digitized DSST device 102 in the version 1 of the digitized DSST. The query digit-symbol appears at the center of the screen. The examinee is asked to undergo the test. If the digit-symbol pair shown in the middle of the screen matches with the entries in the lookup table, the examinee presses the "space bar" button. For the non-matching pair, the examinee should wait for 3 seconds. The waiting response of the examinee is taken as a correct response for the non-matching symbol-digit pair. For every correct decision, the score is incremented. In an example embodiment, the number of digit-symbol pair trial is fixed to 50 and the delay between the disappearance of the previous query digit-symbol pair and the new query digit-symbol pair is 300 milliseconds. The digitized DSST can be adapted to any regional language for the numerals. Further, response time per trial, total time, correctness score and insights drawn from the physiological sensors are measured from the digitized DSST. The insights drawn from the physiological sensors are cognitive load, anxiety, attention and the like. The insights are used to detect the motivation and involvement of the examinee during the entire digital DSST. The motivation and the involvement of the examinee is considered as important since the score calculated during the digitized DSST does not give the true reflection of the behavior of the examinee if there is no involvement. The features, response time per trial, total time, correctness score and insights drawn from the physiological sensors gives valuable information about the neuropsychological condition of the examinee. For example, the time spent in the lookup area, QA and time wander are determined as follows:

Time_LUA:
a) Extract the gaze data lying in L using the boundary information (R).
b) Compute the time spent in LUA as,
Time_LUA=(|R|)/f s; where |R| is the no. of data points in R and fs is the sampling rate of the eye tracker.

Time_QA:
a) Extract the gaze data lying in Q using the boundary information (R).
b) Compute the time spent in Q as,
Time_QA=(|R|)/fs; where |R| is the no. of data points in R and fs is the sampling rate of the eye tracker.

Time_wander:
a) Extract the gaze data (R) not lying in L and Q using the boundary information.
b) Compute the time spent in NROI as,
Time_wander=(|R|)/fs; where |R| is the no. of data points in R and fs is the sampling rate of the eye tracker.

The DSST module 112 then analyzes neuropsychological condition of the examinee using the response time per trial, total time, correctness score and the insights drawn from the physiological sensors. In other words, the DSST module 112 determines memory related functions using the version 1. Since the lookup table entries are fixed in version 1, the examinee tend to remember the symbols with their corresponding numbers. The DSST module 112 determined the memory related functions based on a number of transitions made from the query area (QA) to the lookup area (LUA) and the QA to the target LUA (TLUA). This can be used to derive the memorization index which is inversely proportional to the no. of transitions. For example, the DSST module 112 determines the transition made from the QA to the LUA using the following procedure.

a) Extract the gaze data corresponding to a trial (R).
b) Extract scanpath array (S). Check the (x,y) values in R; if it falls in Q, dump 10, if it falls in NROI then dump 0; if it falls in any region in LUA then dump the corresponding digit value (1 through 9). Hence, S consists of numerical array of size equal to R.
c) Determined diff(trans) #take difference between the current and the previous element in the array (C). This is done to avoid consecutive same elements.
d) Discard off the occurrences of zero in C.
e) Trans QA-→LUA=sum(C) #add all the 1s in C.

For example, the DSST module 112 determines the transition made from the LUA to the QA using the following procedure.

a) Extract the gaze data corresponding to a trial (R).
b) Extract scanpath array (S). Check the (x,y) values in R; if it falls in Q, dump 10, if it falls in NROI then dump 0; if it falls in any region in LUA then dump the corresponding digit value (1 through 9). Hence, S consists of numerical array of size equal to R. Let nT be the id of the T_LUA for a given trial c) Determine diff(trans) #take difference between the current and the previous element in the array (C). This is done to avoid consecutive same elements.
d) Discard off the occurrences of zero in C.
e) Trans QA-→ T_LUA=sum(C) #add all the is in C.

Figure 3A:
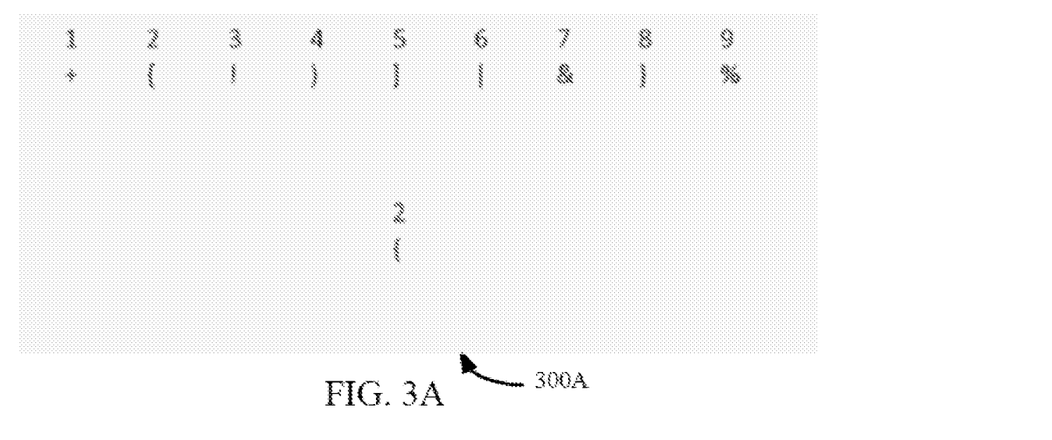
FIG. 3A and FIG. 3B depicts the version 2 of the digitization scheme of DSST, in accordance with an example embodiment of the present disclosure.
Figure 3B:
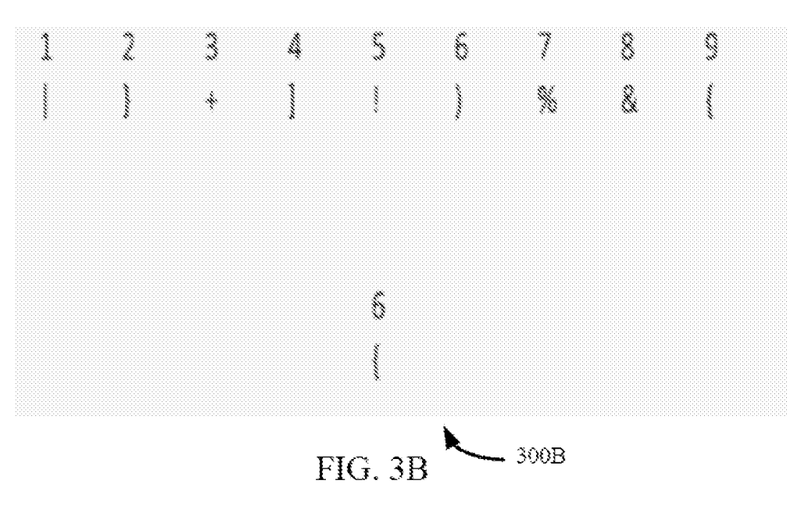

Further, the DSST module 112 trains the examinee with version 2 of the digitized DSST, as shown in FIGS. 3A and 3B. The version 2 is similar to version 1 except that the symbol entries in the lookup table changes with the trial. In version 2, the effect of memorization is nullified as there is no provision to retain the digit-symbol pair in mind. Hence, the physiological changes involved are due to the working memory load. This can be used to derive the index of cognitive activity. For example, the nature of eye movement is one of the main cognitive deficits in Schizophrenic subjects. In an example implementation, the DSST module 112 analyzes nature of eye movement of the examinee in the one of the multiple trials based on the length of the path traversed by eyes of the examinee from the QA pair to the target location in the lookup area and a length of shortest path between the QA pair and the target location in the lookup area. In this example, the DSST module 112 derive the features (e.g., degree centrality, link density, clustering coefficient, and diameter) from the scanpath obtained by the gaze analysis in each trial. In an embodiment, the DSST module 112 extracts eye gaze data (x,y) per trial and derives a scan path S which contains the transitions from the 9 locations in the LUA, QA and the NROI. This array is then used to construct an adjacency matrix A and then the following graph related features are computed.

1) Degree centrality: The degree centrality of a vertex v, for a given graph G:=(V,E) with |V| vertices and |E| edges, is defined as, $C_D(v)=\deg(v)$.
   In other words, Degree centrality of a node=sum of indegrees+sum of outdegrees
2) Link density=2*num_edges/(num_nodes*(num_nodes−1))
3) Clustering coefficient: The clustering coefficient for a given graph G:=(V,E) with v∈V vertices is defined as, $$cc1(v) = \frac{\text{number of pairs of neighbors connected by edges}}{\text{number of pairs of neighbors}}$$

The DSST module 112 computes the clustering coefficient for a graph G by simple averaging of cc1(v) for all v∈V.

4) Diameter: Length of the shortest path between the most distanced nodes. The diameter d of a graph is the maximum eccentricity of any vertex in the graph, i.e., d is the greatest distance between any pair of vertices.

Further, the DSST module 112 determines a scanning index using the derived features. The smaller the value of this index, the lesser is the eye movement. For example, the scanning index is determined using the following equation.

$$\text{scanning index} = \frac{\text{length of the shortest path between the } QA \to TLUA}{\text{length of the path traversed by the eyes from the } QA \to TLUA}$$

Figure 4A:
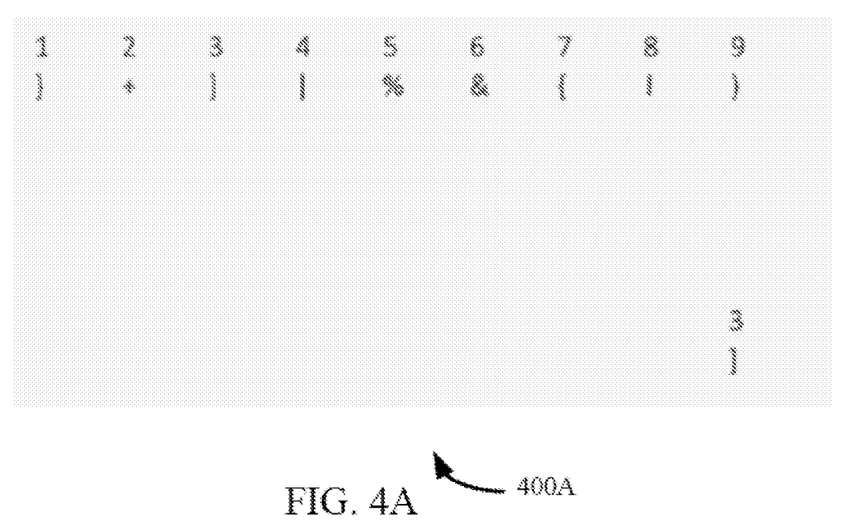
FIG. 4A and FIG. 4B depicts the proposed version 3 of the digitization scheme of DSST, in accordance with an example embodiment of the present disclosure.
Figure 4B:
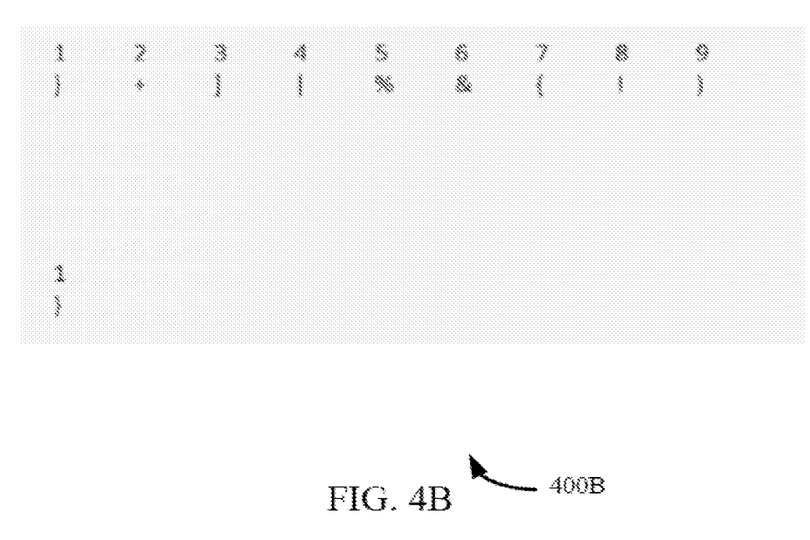

In addition, the DSST module 1122 trains the examinee with version 3 of the DSST, as shown in FIGS. 4A and 4B. In version 3, the QA keeps changing its location with trials. This forces the subject to perform a dual search-locating the position of the QA and then finding the TLUA. The defects like visual neglect can be tracked using this version. Also, this adds additional load on the subject and hence, this version could be compared with version 1 and 2 for changes in the load imposed on the subject. In version 1 and 2, the QA was positioned in the center, but in version 3 it moves away from the center. Hence, this can be used to derive the index of visuo-spatial neglect that is based on the accuracy and response time in matching the query-symbol pair against the lookup table with the increase in distance of the QA from the center of the screen.

Figure 5:
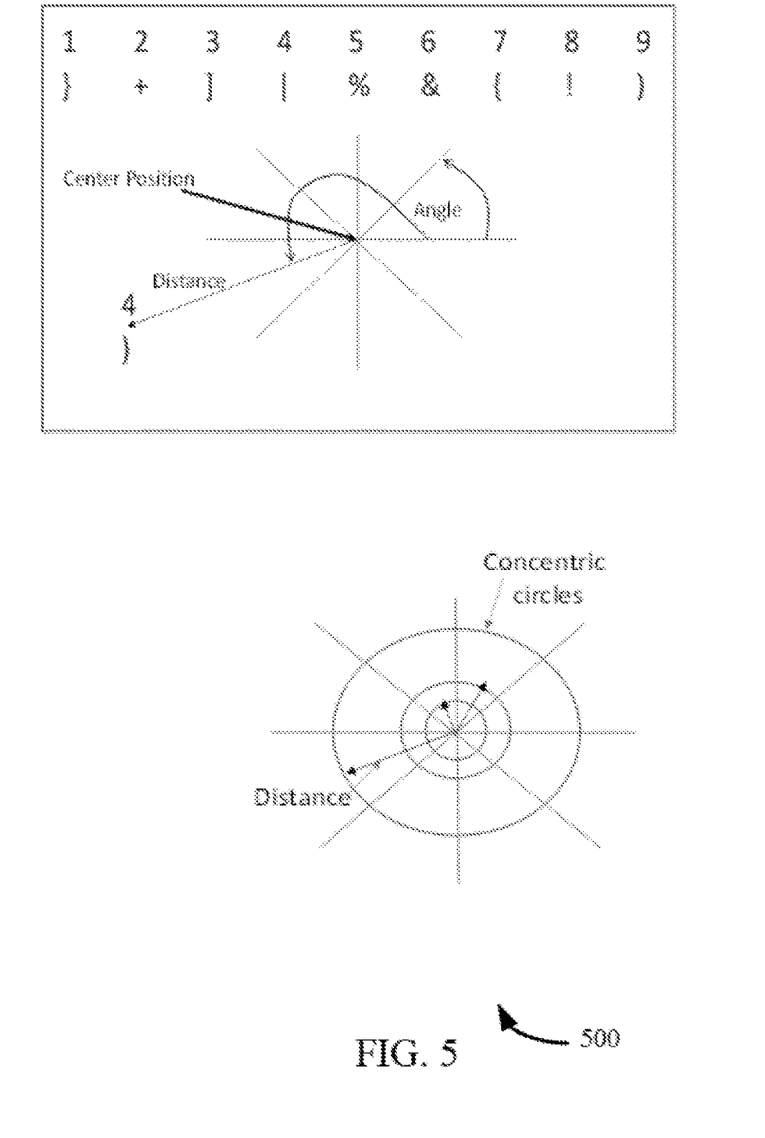
FIG. 5 depicts partitioning of a display area of the DSST device, in accordance with an example embodiment of the present disclosure.
Figure 6:
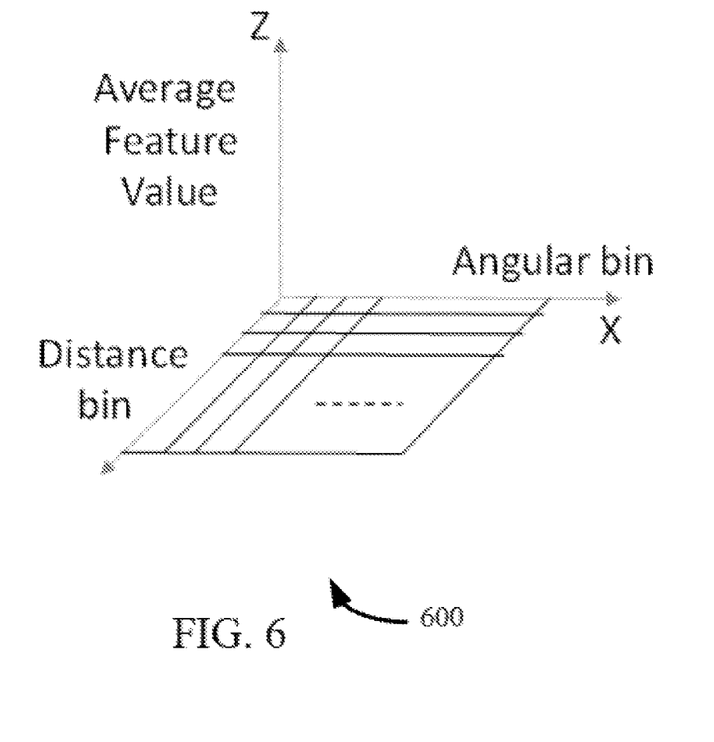
FIG. 6 depicts a graph illustrating multiple bins and average feature values, in accordance with an example embodiment of the present disclosure.

In an example implementation, around the center position of a display area of the DSST device 102, the DSST module 112 divides the 360 degree into N angular bins. Further, the DSST module divides the distance from the center position into M bins using concentric circles. This is shown in FIG. 5. The design of the positions of the query symbol pair is such that there are equal number of pairs in all the bins for both angular and distance bins. Furthermore, the DSST module 112 computes an average response times and accuracy of response (through the spacebar) for the query symbol pair in each bin. As shown in a graph 600 of FIG. 6, the angular bins are plotted in X axis, the distance bins are plotted in Y axis and the average feature values are plotted in Z axis. There are M×N entries in the average feature values. Moreover, the DSST module 112 computes probabilities ($p_{ij}$) in each bin from the average feature values using normalization such that the sum of all the M×N entries is 1, where 1<=i<=M and 1<=j<=N. Also, the DSST module 112 computes the Shannon Entropy from the probabilities of M×N bins using the following equation.

$$H = \Sigma_{i,j=1}^{i=M,j=N} -p_{ij} \log_2 2^{(pij)}$$

The maximum value of H is $\log_2(M*N)$ when all the bins are equally probable, indicating no visual neglect. The least value of H is 0 when any one bin has probability of 1, indicating maximum visual neglect. Thus index of visuo-spatial neglect is $1-H/\log_2(M*N)$, where its range is between 0 and 1. This index gives information on how a feature (e.g. response time, accuracy, eyegaze and scan path related direct or derived features etc.) is distributed over visual space (i.e., the display area). If it is evenly distributed then the Index $(1-H/\log_2(M*N))$ is close to 0 (indicative of no visuospatial neglect), else if it is unevenly distributed to a maximum extend then the index is close to 1 (indicative of high visuospatial neglect).

Figure 7:
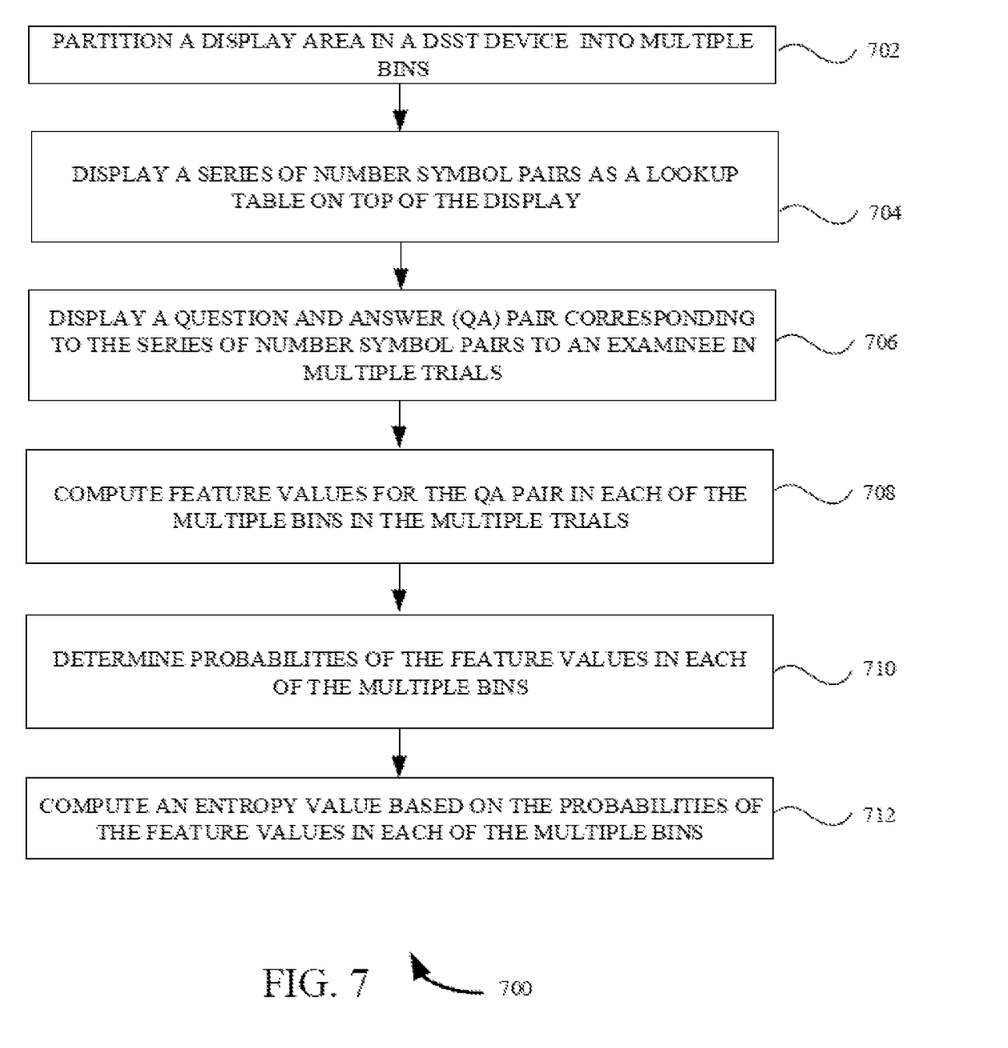
FIG. 7 is a flow diagram illustrating a method for digitized DSST, in accordance with an example embodiment of the present disclosure.

FIG. 7 is a flowchart illustrating a method for digitized DSST, according to an embodiment of a present subject matter. The processor-implemented method 700 may be described in the general context of computer executable instructions. Generally, computer executable instructions can include routines, programs, objects, components, data structures, procedures, modules, functions, etc., that perform particular functions or implement particular abstract data types. The method 700 may also be practiced in a distributed computing environment where functions are performed by remote processing devices that are linked through a communication network. The order in which the method 700 is described is not intended to be construed as a limitation, and any number of the described method blocks can be combined in any order to implement the method 700, or an alternative method. Furthermore, the method 700 can be implemented in any suitable hardware, software, firmware, or combination thereof. In an embodiment, the method 700 depicted in the flow chart may be executed by a system, for example, the system 100 of FIG. 1.

At block 702, a display area of a digitized digit symbol substitution test (DSST) device is partitioned into multiple bins based on distance and degree from a center position of the display area. In an example embodiment, around the center position of the display area, 360 degree is partitioned into a first set of the multiple bins. Further, distance from the center position is partitioned into remaining set of the multiple bins using concentric circles.

At block 704, a series of number symbol pair as a lookup table on top of the display area, termed as lookup area. At block 706, a question and answer (QA) pair corresponding to the series of number symbol pairs is displayed on the digitized DSST device to an examinee in multiple trials, where the location of the QA pair is changed in each of the multiple trials so that equal number of pairs are present in the multiple bins. At block 708, feature values for the QA pair are computed in each of the multiple bins in the multiple trials when target location is identified. The target location in the lookup table is termed as the number symbol pair in the lookup table for which the number matches with the number of the number symbol pair of the QA. For example, the feature values include a response time and an accuracy of response by the examinee. In an example embodiment, the examinee is enabled to provide input for the QA pair in each of the multiple bins in each of the multiple trials through a spacebar in the digitized DSST device. Further, the feature values are computed for the QA pair in each of the multiple bins in the multiple trials upon receiving the input from the examinee for the QA pair in each of the multiple bins in each of the multiple trials.

At block 710, probabilities of the feature values are determined in each of the multiple bins. In an embodiment, an average of the feature values is determined in each of the multiple bins. Further, the probabilities of the average of the feature values in each of the multiple bins is determined using normalization.

At block 712, an entropy value is computed based on the probabilities of the feature values in each of the multiple bins, the entropy value provides information on distribution of the feature values in the display area. The entropy value is maximum when the distribution of the feature values in the display area is probable and wherein the entropy value is minimum when the distribution of the feature values in the display area is not probable.

In some embodiments, a length of a path traversed by eyes of the examinee from a QA pair to the target location in the lookup area is computed in one of the multiple trials. Further, nature of eye movement (i.e., speed of processing) of the examinee in the one of the multiple trials based on the length of the path traversed by eyes of the examinee from the QA pair to the target location in the lookup area and a length of shortest path between the QA pair and the target location in the lookup area. This is explained in more detail with reference to FIG. 1.

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

It is, however to be understood that the scope of the protection is extended to such a program and in addition to a computer-readable means having a message therein; such non-transitory computer-readable storage means contain program-code means for implementation of one or more steps of the method, when the program runs on a server or mobile device or any suitable programmable device. The hardware device can be any kind of device which can be programmed including e.g. any kind of computer like a server or a personal computer, or the like, or any combination thereof. The device may also include means which could be e.g. hardware means like e.g. an application-specific integrated circuit (ASIC), a field-programmable gate array (FPGA), or a combination of hardware and software means, e.g. an ASIC and an FPGA, or at least one microprocessor and at least one memory with software modules located therein. Thus, the means can include both hardware means and software means. The method embodiments described herein could be implemented in hardware and software. The device may also include software means. Alternatively, the embodiments may be implemented on different hardware devices, e.g. using a plurality of CPUs.

The embodiments herein can comprise hardware and software elements. The embodiments that are implemented in software include but are not limited to, firmware, resident software, microcode, etc. The functions performed by various modules described herein may be implemented in other modules or combinations of other modules. For the purposes of this description, a computer-usable or computer readable medium can be any apparatus that can comprise, store, communicate, propagate, or transport the program for use by or in connection with the instruction execution system, apparatus, or device.

The foregoing description of the specific implementations and embodiments will so fully reveal the general nature of the implementations and embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the embodiments as described herein.

The preceding description has been presented with reference to various embodiments. Persons having ordinary skill in the art and technology to which this application pertains will appreciate that alterations and changes in the described structures and methods of operation can be practiced without meaningfully departing from the principle, spirit and scope.

We claim:

1. A processor-implemented method comprising:
    partitioning a display area of a digitized digit symbol substitution test (DSST) device into multiple bins based on distance and degree from a center position of the display area;
    displaying a series of number symbol pairs as a lookup table on top of the display, termed as a lookup area;
    displaying a question and answer (QA) pair corresponding to the series of number symbol pairs to an examinee in multiple trials, wherein the location of the QA pair is changed in each of the multiple trials so that equal number of pairs are present in the multiple bins;

computing feature values for the QA pair in each of the multiple bins in the multiple trials, wherein the feature values comprise a response time and an accuracy of response by the examinee;

determining probabilities of the feature values for each of the multiple bins;

computing an entropy value based on the probabilities of the feature values for each of the multiple bins, wherein the entropy value provides information on distribution of the feature values in the display area;

measuring, by a plurality of sensors attached to the examinee, a plurality of physiological changes in the examinee during the multiple trails, wherein the plurality of sensors include an eye tracker, a galvanic skin response (GSR) sensor, a electroencephalogram (EEG) sensor, a photoplethysmography (PPG) sensor and a peripheral capillary oxygen saturation (SpO2) sensor, and wherein measuring the physiological changes in the examinee involves:
- computing a length of a path traversed by eyes of the examinee from a QA pair to a target location in the lookup area in one of the multiple trials; and
- analyzing speed of processing of the examinee in the one of the multiple trials based on the length of the path traversed by eyes of the examinee from the QA pair to the target location in the lookup area and a length of shortest path between the QA pair and the target location in the lookup area; and determining a neuropsychological condition of the examinee based on the feature values, the entropy value, and the physiological changes in the examinee.

2. The method as claimed in claim 1, wherein partitioning the display area of the digitized DSST device into the multiple bins based on distance and degree from the center position of the display area, comprises:
- around the center position of the display area, partitioning 360 degree into a first set of the multiple bins; and
- partitioning distance from the center position into remaining set of the multiple bins using concentric circles.

3. The method as claimed in claim 1, wherein computing the feature values for the QA pair in each of the multiple bins in the multiple trials, wherein the feature values comprise the response time and accuracy of response by the examinee, comprises:
- enabling the examinee to provide input for the QA pair in each of the multiple bins in each of the multiple trials through a spacebar in the digitized DSST system; and
- computing the feature values for the QA pair in each of the multiple bins in the multiple trials upon receiving the input from the examinee for the QA pair in each of the multiple bins in each of the multiple trials.

4. The method as claimed in claim 1, wherein determining the probabilities of the feature values for each of the multiple bins, comprises:
- determining an average of the feature values for each of the multiple bins; and
- determining the probabilities of the average of the feature values for each of the multiple bins.

5. The method as claimed in claim 1, wherein determining the probabilities of the feature values for each of the multiple bins, comprises:
- determining the probabilities of the feature values for each of the multiple bins using normalization.

6. The method as claimed in claim 1, wherein the entropy value is maximum when the distribution of the feature values in the display area is probable and wherein the entropy value is minimum when the distribution of the feature values in the lookup area is not probable.

7. The method as claimed in claim 1, wherein the target location in the lookup table is termed as the number symbol pair in the lookup table for which the number matches with the number of the number symbol pair of the QA.

8. A system comprising:
- a digitized digit symbol substitution test (DSST) device, wherein the DSST device comprises:
- one or more memories; and
- one or more hardware processors, the one or more memories coupled to the one or more hardware processors, wherein the one or more hardware processors are capable of executing programmed instructions stored in the one or more memories to:
  - partition a display area in the DSST device into multiple bins based on distance and degree from a center position of the display area;
  - display a series of number symbol pairs as a lookup table on top of the display, termed as a lookup area;
  - display a question and answer (QA) pair corresponding to the series of number symbol pairs to an examinee in multiple trials, wherein the location of the QA pair is changed in each of the multiple trials so that equal number of pairs are present in the multiple bins;
  - compute feature values for the QA pair in each of the multiple bins in the multiple trials, wherein the feature values comprise a response time and an accuracy of response by the examinee;
  - determine probabilities of the feature values for each of the multiple bins;
  - compute an entropy value based on the probabilities of the feature values for each of the multiple bins, wherein the entropy value provides information on distribution of the feature values in the display area;
  - measure, by a plurality of sensors attached to the examinee, a plurality of physiological changes in the examinee during the multiple trails, wherein the plurality of sensors include an eye tracker, a galvanic skin response (GSR) sensor, a electroencephalogram (EEG) sensor, a photoplethysmography (PPG) sensor and a peripheral capillary oxygen saturation (SpO2) sensor, and wherein measuring the physiological changes in the examinee involves:
    - computing a length of a path traversed by eyes of the examinee from a QA pair to a target location in the lookup area in one of the multiple trials; and
    - analyzing speed of processing of the examinee in the one of the multiple trials based on the length of the path traversed by eyes of the examinee from the QA pair to the target location in the lookup area and a length of shortest path between the QA pair and the target location in the lookup area; and
  - determine a neuropsychological condition of the examinee based on the feature values, the entropy value, and the physiological changes in the examinee.

9. The system as claimed in claim 8, wherein one or more hardware processors are capable of executing programmed instructions to:
- around the center position of the display area, partition 360 degree into a first set of the multiple bins; and
- partition distance from the center position into remaining set of the multiple bins using concentric circles.

10. The system as claimed in claim 8, wherein one or more hardware processors are capable of executing programmed instructions to:
enable the examinee to provide input for the QA pair in each of the multiple bins in each of the multiple trials through a spacebar in the digitized DSST system; and
compute the feature values for the QA pair in each of the multiple bins in the multiple trials upon receiving the input from the examinee for the QA pair in each of the multiple bins in each of the multiple trials.

11. The system as claimed in claim 8, wherein one or more hardware processors are capable of executing programmed instructions to:
determine an average of the feature values for each of the multiple bins; and
determine the probabilities of the average of the feature values for each of the multiple bins.

12. The system as claimed in claim 8, wherein one or more hardware processors are capable of executing programmed instructions to:
determine the probabilities of the feature values for each of the multiple bins using normalization.

13. The system as claimed in claim 8, wherein the entropy value is maximum when the distribution of the feature values in the display area is probable and wherein the entropy value is minimum when the distribution of the feature values in the display area is not probable.

14. The system as claimed in claim 8, wherein the target location in the lookup table is termed as the number symbol pair in the lookup table for which the number matches with the number of the number symbol pair of the QA.

15. A computer program product comprising a non-transitory computer readable medium having a computer readable program embodied therein, wherein the computer readable program, when executed on a computing device, causes the computing device to:
partition a display area of a digitized digit symbol substitution test (DSST) device into multiple bins based on distance and degree from a center position of the display area;
display a series of number symbol pairs as a lookup table on top of the display, termed as a lookup area;
display a question and answer (QA) pair corresponding to the series of number symbol pairs to an examinee in multiple trials, wherein the location of the QA pair is changed in each of the multiple trials so that equal number of pairs are present in the multiple bins;
compute feature values for the QA pair in each of the multiple bins in the multiple trials, wherein the feature values comprise a response time and an accuracy of response by the examinee;
determine probabilities of the feature values for each of the multiple bins;
compute an entropy value based on the probabilities of the feature values for each of the multiple bins, wherein the entropy value provides information on distribution of the feature values in the display area;
measuring, by a plurality of sensors attached to the examinee, a plurality of physiological changes in the examinee during the multiple trails, wherein the plurality of sensors include an eye tracker, a galvanic skin response (GSR) sensor, a electroencephalogram (EEG) sensor, a photoplethysmography (PPG) sensor and a peripheral capillary oxygen saturation (SpO2) sensor, and wherein measuring the physiological changes in the examinee involves:
computing a length of a path traversed by eyes of the examinee from a QA pair to a target location in the lookup area in one of the multiple trials; and
analyzing speed of processing of the examinee in the one of the multiple trials based on the length of the path traversed by eyes of the examinee from the QA pair to the target location in the lookup area and a length of shortest path between the QA pair and the target location in the lookup area; and
determining a neuropsychological condition of the examinee based on the feature values, the entropy value, and the physiological changes in the examinee.

\* \* \* \* \*